United States Patent
Billot et al.

(10) Patent No.: US 8,378,128 B2
(45) Date of Patent: Feb. 19, 2013

(54) CRYSTALLINE FORMS OF DIMETHOXY DOCETAXEL AND METHODS FOR PREPARING THE SAME

(75) Inventors: Pascal Billot, Paris (FR); Marielle Dufraigne, Paris (FR); Hagit Elmaleh, Paris (FR); Alexandre Giuliani, Paris (FR); Fabrice Mangin, Paris (FR); Patricia Rortais, Paris (FR); Lionel Zaske, Paris (FR)

(73) Assignee: Aventis Pharma SA, Antony (FR)

( * ) Notice: Subject to any disclaimer, the term of this patent is extended or adjusted under 35 U.S.C. 154(b) by 0 days.

(21) Appl. No.: 12/837,559

(22) Filed: Jul. 16, 2010

(65) Prior Publication Data

US 2011/0144362 A1    Jun. 16, 2011

Related U.S. Application Data

(63) Continuation of application No. PCT/FR2009/000042, filed on Jan. 15, 2009.

(30) Foreign Application Priority Data

Jan. 17, 2008  (FR) .................................. 08 00243

(51) Int. Cl.
*C07D 305/14*    (2006.01)
(52) U.S. Cl. ....................................................... 549/510
(58) Field of Classification Search .................... 549/510
See application file for complete search history.

(56) References Cited

U.S. PATENT DOCUMENTS 5,847,170 A * 12/1998 Bouchard et al. ............. 549/510
6,346,543 B1 * 2/2002 Bissery et al. ................ 514/449
7,241,907 B2 * 7/2007 Didier et al. .................. 549/510

FOREIGN PATENT DOCUMENTS

WO    WO 96/30355    3/1996
WO    WO 2005028462    3/2005

OTHER PUBLICATIONS

Bryn et al, Solid State Chemistry of Drugs, 2nd edition, 1999, SSCI, Inc. Chapter 10, Polymorphs, p. 232-247.*
Chawla, Crips, vol. 5, No. 1, Jan.-Mar. 2004, p. 9-12.*
Rodriquez-Spong et al, 2004, Advanced Drug Delivery Reviews, vol. 56, p. 241-274.*
Souillac et al, Encyclopedia of Controlled Drug Delivery, 1999, John Wiley & Sons, p. 212-227.*
International Search Report for WO2009115655 dated Sep. 24, 2009.
Mino R. Caira, Crystalline Polymorphism of Organic Compounds, Topics in Current Chemistry, (1998, pp. 163-208, vol. 198).

* cited by examiner

*Primary Examiner* — Golam M M Shameem
*Assistant Examiner* — Karen Cheng
(74) *Attorney, Agent, or Firm* — Brian R. Morrill

(57) ABSTRACT

The invention relates to anhydrides, solvates and ethanol hetero-solvates and hydrates of dimethoxy docetaxel or (2R, 3S)-3-tert-butoxycarbonylamino-2-hydroxy-3-phenyl-propionate of 4-acetoxy-2α-benzoyloxy-5β,20-epoxy-1-hydroxy-7β, 10β-dimethoxy-9-oxo-tax-11-ene-13α-yl, and to the preparation thereof.

1 Claim, 5 Drawing Sheets

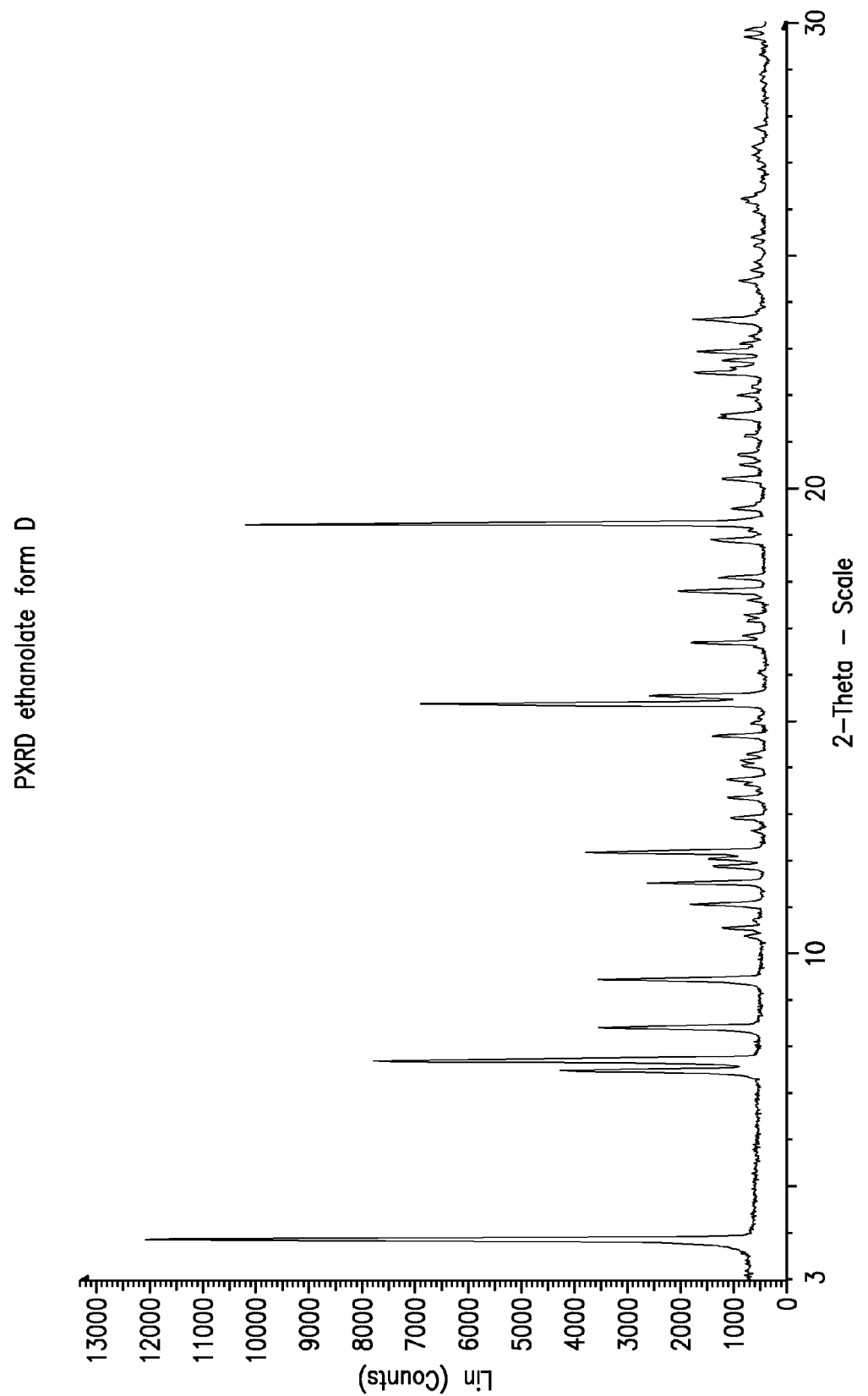

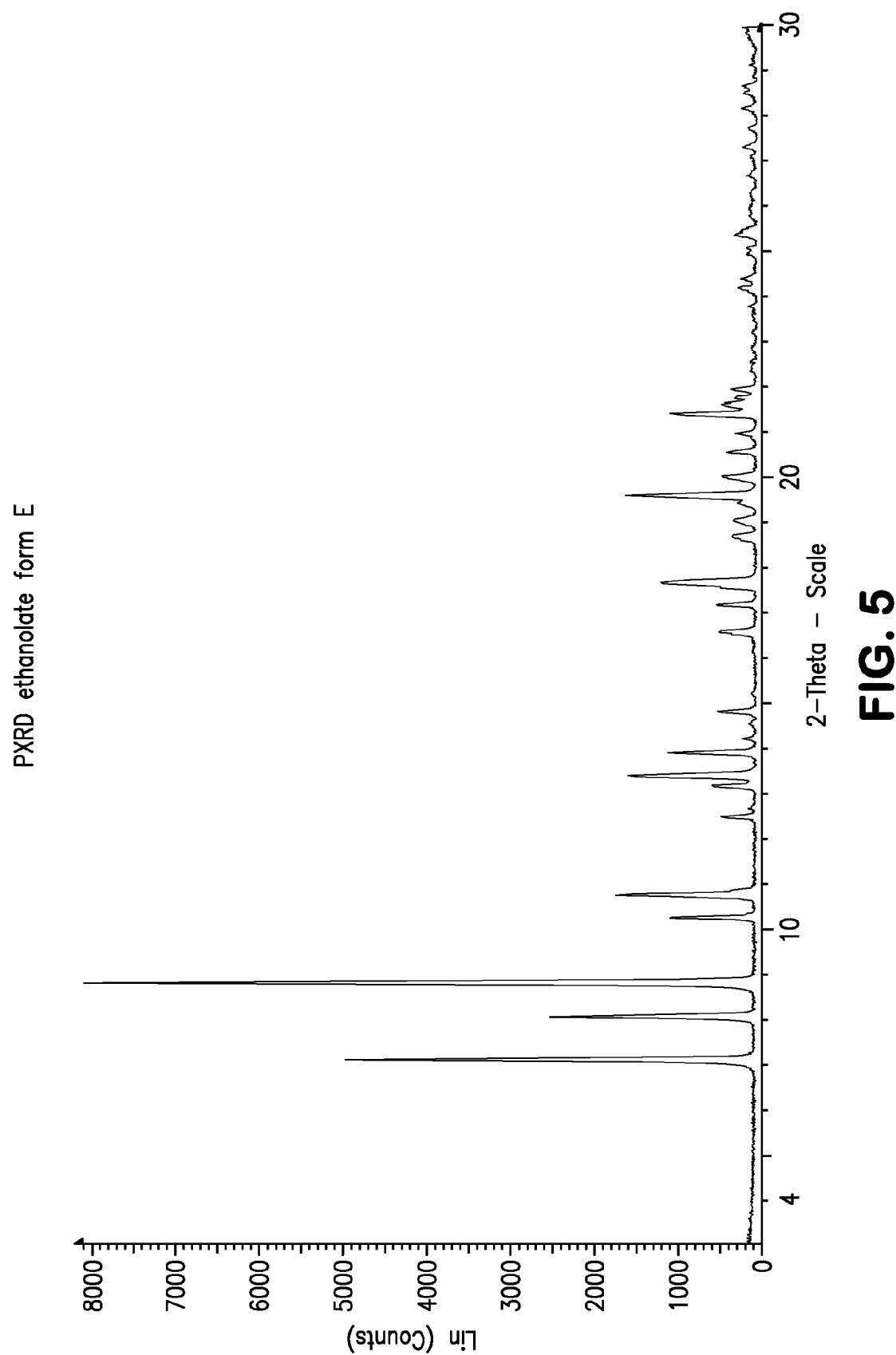

CRYSTALLINE FORMS OF DIMETHOXY DOCETAXEL AND METHODS FOR PREPARING THE SAME

The present invention relates to crystalline forms of dimethoxy docetaxel or 4-acetoxy-2α-benzoyloxy-5β,20-epoxy-1-hydroxy-7β,10β-dimethoxy-9-oxotax-11-en-13α-yl (2R,3 S)-3-tert-butoxycarbonylamino-2-hydroxy-3-phenylpropionate and to methods for the preparation thereof.

BACKGROUND OF THE INVENTION

4-Acetoxy-2α-benzoyloxy-5β,20-epoxy-1-hydroxy-7β,10β-dimethoxy-9-oxotax-11-en-13α-yl (2R,3S)-3-tert-butoxycarbonylamino-2-hydroxy-3-phenylpropionate exhibits notable anticancer and antileukaemic properties.

4-Acetoxy-2α-benzoyloxy-5β,20-epoxy-1-hydroxy-7β,10β-dimethoxy-9-oxotax-11-en-13α-yl (2R,3S)-3-tert-butoxycarbonylamino-2-hydroxy-3-phenylpropionate is prepared according to the method which is described more particularly in PCT International Application WO 96/30355 or PCT International Application WO 99/25704. According to the method described in these applications, the product is not crystallized and is not characterized.

It was found that the acetone solvate of 4-acetoxy-2α-benzoyloxy-5β,20-epoxy-1-hydroxy-7β,10β-dimethoxy-9-oxotax-11-en-13α-yl (2R,3S)-3-tert-butoxycarbonylamino-2-hydroxy-3-phenylpropionate (called form A) was completely determined and characterized according to the patent published under number WO2005/028462.

BRIEF SUMMARY OF THE INVENTION

The present invention relates to new crystalline forms, with the exclusion of the acetonate form, the only one known to date.

According to the present invention, it has now been found that certain anhydrous forms, certain ethanolic solvates or heterosolvates and hydrated forms have been completely characterized from a physical and chemical structure point of view.

BRIEF DESCRIPTION OF THE DRAWINGS

FIG. 4 depicts a Powder X-Ray Diffraction (PXRD) analysis for ethanolate form D.

FIG. 5 depicts a Powder X-Ray Diffraction (PXRD) analysis for ethanolate form E.

DETAILED DESCRIPTION OF THE INVENTION

According to the invention, among the anhydrous forms of 4-acetoxy-2α-benzoyloxy-5β,20-epoxy-1-hydroxy-7β,10β-dimethoxy-9-oxotax-11-en-13α-yl (2R,3S)-3-tert-butoxycarbonylamino-2-hydroxy-3-phenylpropionate, five different forms have been identified, among the ethanolic solvates or heterosolvates of 4-acetoxy-2α-benzoyloxy-5β,20-epoxy-1-hydroxy-7β,10β-dimethoxy-9-oxotax-11-en-13α-yl (2R,3S)-3-tert-butoxycarbonylamino-2-hydroxy-3-phenylpropionate, four different forms have been identified and among the hydrates of 4-acetoxy-2α-benzoyloxy-5β,20-epoxy-1-hydroxy-7β,10β-dimethoxy-9-oxotax-11-en-13α-yl (2R,3S)-3-tert-butoxycarbonylamino-2-hydroxy-3-phenylpropionate, two different forms have been identified.

The five anhydrous forms identified were obtained according to the following methods:

The anhydrous form B by a method which consists in heating the acetone form or form A obtained according to the patent mentioned above, between 100 and 110° C. under vacuum or nitrogen sweeping. This treatment is preferably carried out for at least 9 hours before a return to ambient temperature without inducing chemical decomposition. Its melting point by DSC is approximately 150° C. The PXRD diagram of the anhydrous form B exhibits characteristic lines located at 7.3, 8.1, 9.8, 10.4, 11.1, 12.7, 13.1, 14.3, 15.4 and 15.9±0.2 degrees 2-theta.

The anhydrous form C is obtained by maturation of the acetone solvate form A, or of the anhydrous form B, in water followed by drying at up to 50° C. and maintaining between 0 and 5% RH at ambient temperature. Its melting point by DSC is approximately 146° C. The PXRD diagram of the anhydrous form C exhibits characteristic lines located at 4.3, 6.8, 7.4, 8.7, 10.1, 11.1, 11.9, 12.3, 12.6 and 13.1±0.2 degrees 2-theta. It is, among the various anhydrous forms, the least stable of all the forms described in the present invention. In the presence of a relative humidity of greater than 5%, it changes to a hydrated form.

Figure 1:
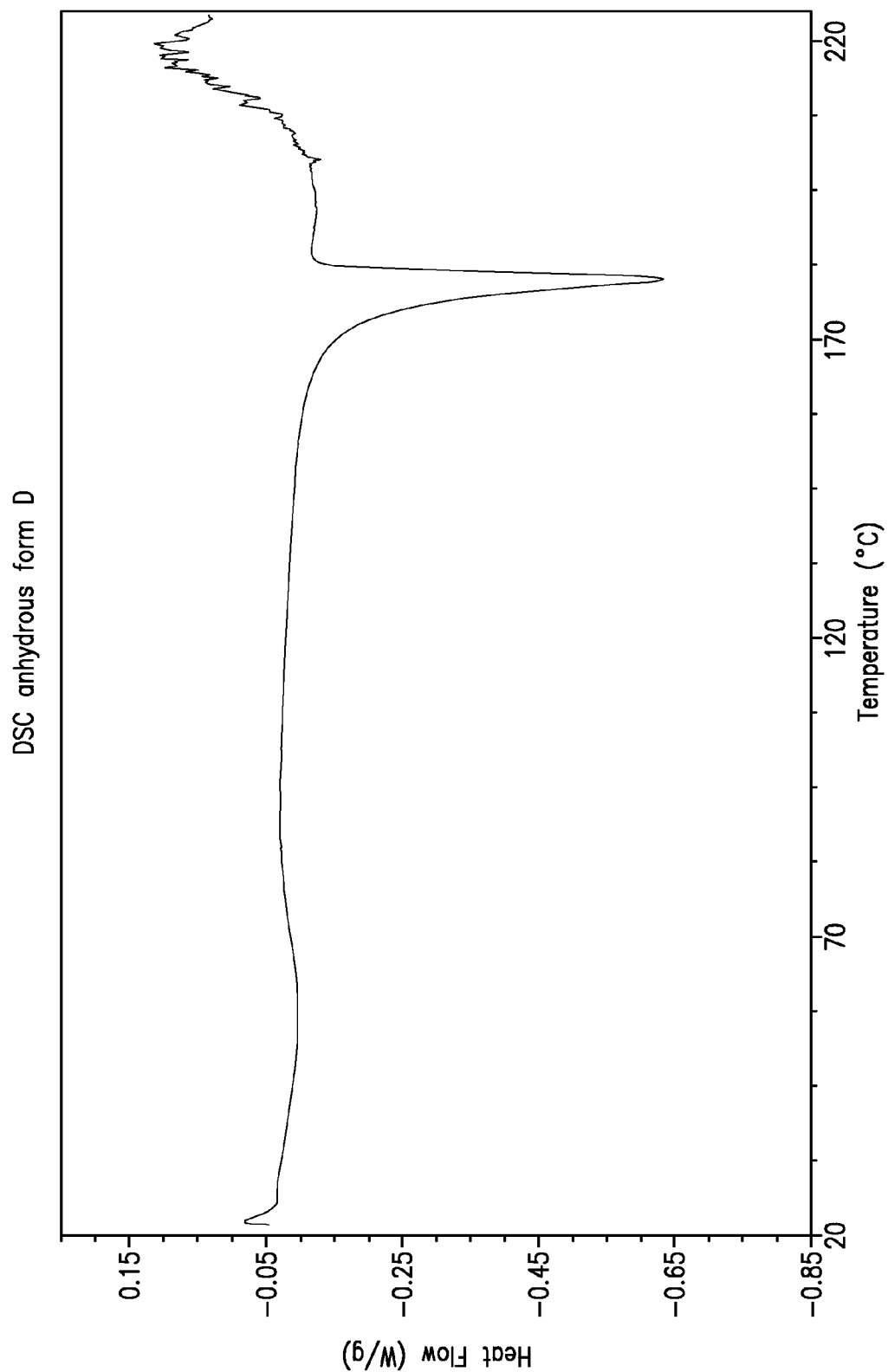
FIG. 1 depicts a Differential Scanning calorimetry (DSC) analysis for anhydrous form D.
Figure 2:
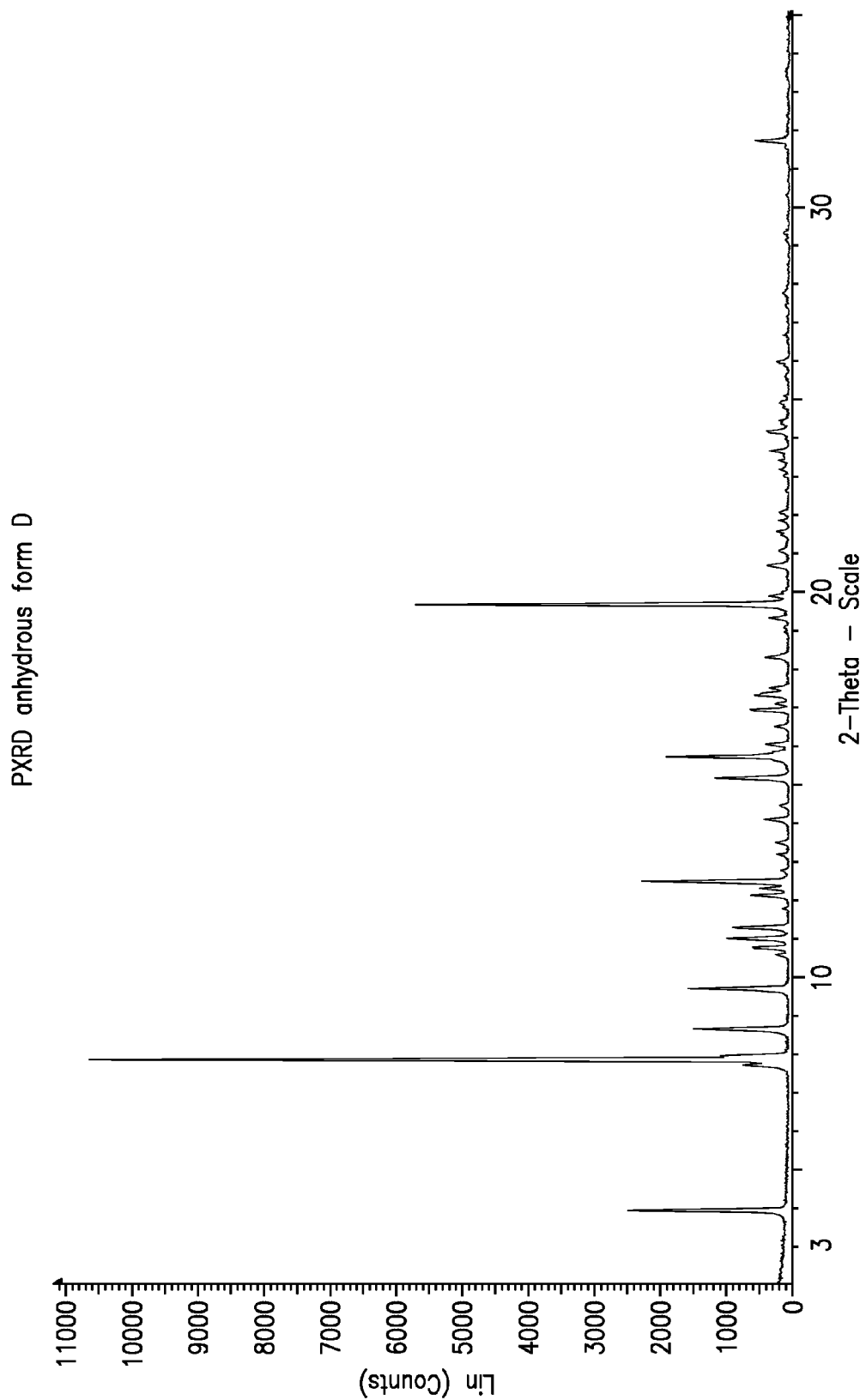
FIG. 2 depicts a Powder X-Ray Diffraction (PXRD) analysis for anhydrous form D.
Figure 3:
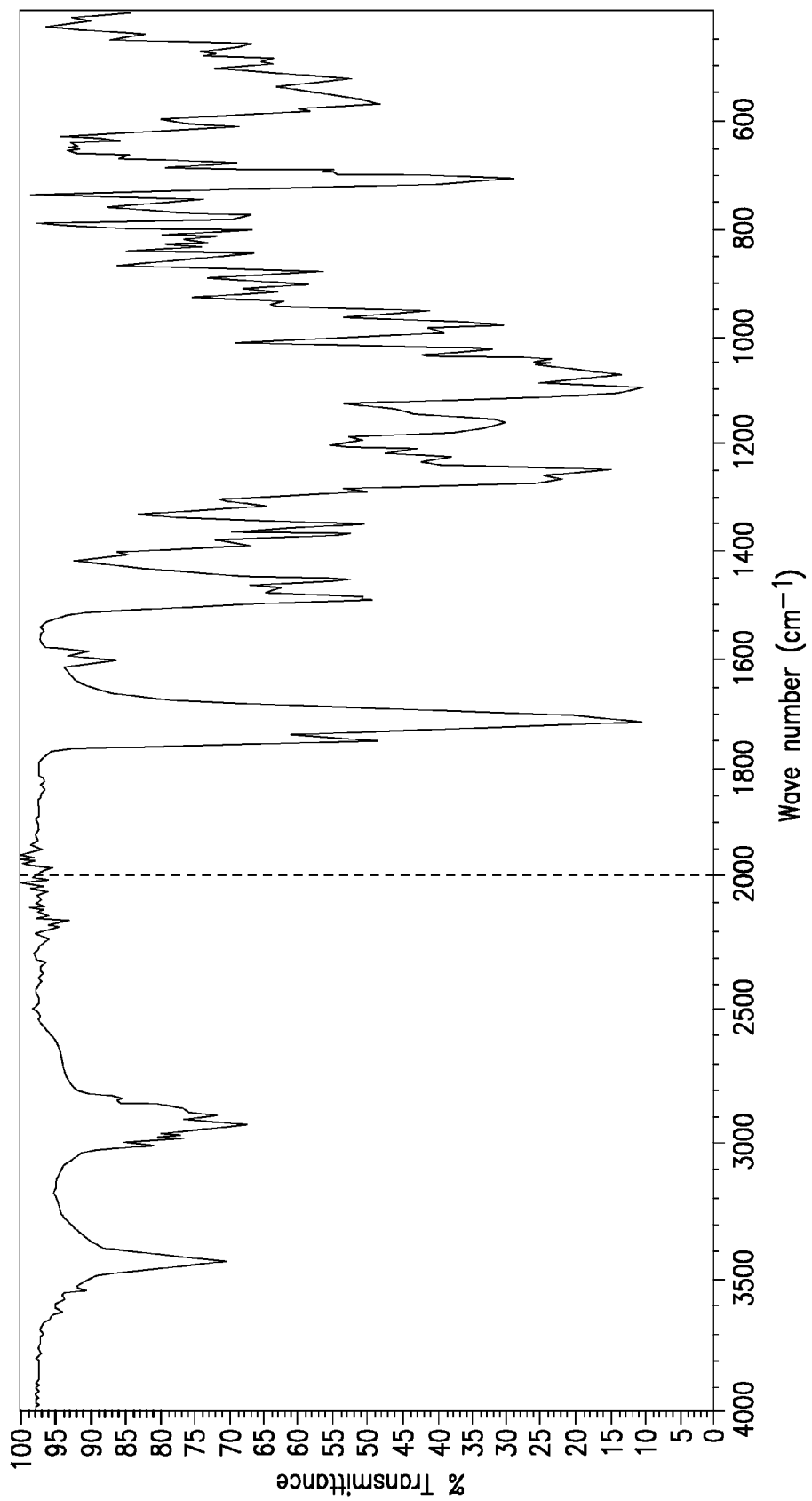
FIG. 3 depicts Fourier Transform InfraRed (FTIR) spectrometry analysis for anhydrous form D.

The anhydrous form D is obtained according to a first method by crystallization of the form A in an oil (especially Miglyol), following by rinsing with an alkane, for example heptane; the second preparation method consists in leaving a solution of 4-acetoxy-2α-benzoyloxy-5β,20-epoxy-1-hydroxy-7β,10β-dimethoxy-9-oxotax-11-en-13α-yl (2R,3S)-3-tert-butoxycarbonylamino-2-hydroxy-3-phenylpropionate in a mixture of Polysorbate 80, pH 3.5, ethanol and water (preferably a 25/25/50 mixture) to crystallize for approximately 48 hours. Its boiling point by DSC is approximately 175° C. (cf. FIG. 1) and is found to be the highest of all the anhydrous forms isolated. The PXRD diagram of the anhydrous form D (cf. FIG. 2) exhibits characteristic lines located at 3.9, 7.7, 7.8, 7.9, 8.6, 9.7, 10.6, 10.8, 11.1 and 12.3±0.2 degrees 2-theta. The FTIR spectrum of the anhydrous form D exhibits characteristic bands located at 979, 1072, 1096, 1249, 1488, 1716, 1747, 3436±1 $cm^{-1}$ (cf. FIG. 3). Among all the forms described in the present invention, it is the most stable anhydrous form.

The anhydrous form E is obtained at ambient temperature by maturation of the acetone form or form A in ethanol so as to intermediately form an ethanolic form which is subsequently desolvated under nitrogen sweeping or by heating at approximately 100° C. for 2 hours. Its melting point by DSC is approximately 157° C. The PXRD diagram of the anhydrous form E exhibits characteristic lines located at 7.1, 8.1, 8.9, 10.2, 10.8, 12.5, 12.7, 13.2, 13.4 and 13.9±0.2 degrees 2-theta.

The anhydrous form F is obtained by desolvating the ethanol/water heterosolvate at 120° C. under a nitrogen atmosphere for 24 hours and then maintaining in a dry environment at 0% RH at ambient temperature. Its melting point by DSC is approximately 148° C. The PXRD diagram of the anhydrous form F exhibits characteristic lines located at 4.4, 7.2, 8.2, 8.8, 9.6, 10.2, 10.9, 11.2, 12.1 and 12.3±0.2 degrees 2-theta.

There are four crystalline forms identified in ethanolic solvate or heterosolvate form:

The ethanolate form B is obtained at ambient temperature by maintaining the anhydrous form B in an ethanol-vapour-saturated environment. The PXRD diagram of the ethanolate form B exhibits characteristic lines located at 7.3, 7.8, 8.8, 10.2, 12.6, 12.9, 13.4, 14.2, 14.7 and 15.1±0.2 degrees 2-theta.

The ethanolate form D is obtained at ambient temperature by maintaining the anhydrous form D in an ethanol-vapour-saturated environment. The PXRD diagram of the ethanolate form D (cf. FIG. 4) exhibits characteristic lines located at 3.8, 7.5, 7.7, 8.4, 9.4, 10.3, 10.5, 11.1, 11.5 and 11.9±0.2 degrees 2-theta.

The ethanolate form E is obtained at ambient temperature by maturation of the acetonate form A in ethanol. The PXRD diagram of the ethanolate form E (cf. FIG. 5) exhibits characteristic lines located at 7.1, 8.1, 8.8, 10.2, 10.7, 12.5, 13.2, 13.4, 13.9 and 14.2±0.2 degrees 2-theta.

The ethanol/water heterosolvate form F is obtained by maintaining the form B in a minimum amount of ethanol at reflux, slow cooling and isolation at ambient temperature and ambient relative humidity. The PXRD diagram of the ethanol/water heterosolvate form F exhibits characteristic lines located at 4.4, 7.2, 8.2, 8.3, 8.8, 9.6, 10.3, 10.9, 11.2 and 12.2±0.2 degrees 2-theta.

There are two crystalline forms identified in hydrate form:

The monohydrated forms C are obtained at ambient temperature by maintaining the anhydrous form C in an atmosphere containing at least 10% relative humidity. The PXRD diagram of the monohydrate form C exhibits characteristic lines located at 4.3, 6.8, 7.4, 8.6, 10.1, 11.1, 11.9, 12.2, 12.6 and 13.3±0.2 degrees 2-theta.

The dihydrate form C is obtained at ambient temperature by maintaining the anhydrous form C in an atmosphere containing at least 60% relative humidity. The PXRD diagram of the dihydrate form C exhibits characteristic lines located at 4.2, 6.9, 7.5, 8.4, 9.9, 10.9, 11.7, 12.3, 12.6 and 13.2±0.2 degrees 2-theta.

Other, nonethanolic, solvates of the form B were prepared, such as in particular those obtained with the following solvents: dichloromethane, diisopropyl ether, n-propanol, isopropanol, toluene, methyl isobutyl ketone, tetrahydrofuran, dimethylformamide, ethyl acetate, etc.

The present invention will be described more fully by means of the following examples which should not be considered to limit the invention.

Experimental Analysis Conditions:

Differential Scanning calorimetry (DSC):

The measurements were carried out on a T.A. Instruments DSC2010 thermal analyser. The sample is subjected to temperature programming from 25° C. to 225° C. with a heating rate of 5° C./min. The product is placed in a crimped aluminium capsule and the amount of product analysed is between 2 and 5 mg. Constant nitrogen sweeping at 55 mL/min is used in the oven chamber.

Powder X-Ray Diffraction (PXRD):

The analyses were carried out on a Panalytical X'Pert Pro diffractometer with a reflection-mode Bragg-Brentano focusing geometry (θ-2θ) assembly. The product analysed is deposited as a thin layer on a silicon single crystal. A copper anticathode tube (45 kV/40 mA) supplies an incident radiation Cu K$\alpha_1$ ($\lambda$=1.5406 Å). The beam is collimated using Sollers slits which improve the parallelism and variable slits which limit scattering. An X'Celerator detector completes the device. The diagram recording characteristics are the following: sweeping from 2 to 30 degrees 2θ, counting time from 100 to 500 seconds per step with a step of 0.017°.

Fourier Transform InfraRed (FTIR) Spectrometry:

The solid samples were analysed using a Nicolet Nexus spectrometer. The analysis is carried out by attenuated total reflectance (ATR) using a Smart Orbit accessory from the company Thermo (single reflection diamond crystal ATR accessory). The spectral range swept is between 4000 and 400 $cm^{-1}$ with a resolution of 2 $cm^{-1}$ and an accumulated scan number of 20.

Example 1

Two tests of dissolution of approximately 550 mg of 4-acetoxy-2α-benzoyloxy-5β,20-epoxy-1-hydroxy-7β,10β-dimethoxy-9-oxotax-11-en-13α-yl (2R,3S)-3-tert-butoxycarbonylamino-2-hydroxy-3-phenylpropionate in 14 g of Miglyol 812 Neutral oil, Sasol are carried out. Magnetic stirring is carried out at 500 rpm for 24 hours at ambient temperature.

After one week, the samples are vacuum-filtered and rinsed with heptane. Each sample is analysed by PXRD for confirmation of the form obtained. After filtration, between 300 and 350 mg of anhydrous form D are obtained.

Example 2

Approximately 3 g of 4-acetoxy-2α-benzoyloxy-5β,20-epoxy-1-hydroxy-7β,10β-dimethoxy-9-oxotax-11-en-13α-yl (2R,3S)-3-tert-butoxycarbonylamino-2-hydroxy-3-phenyl-propionate are dissolved in a mixture of 50 mL ethanol +50 mL Polysorbate 80, pH 3.5. 100 mL of water are added to the previous mixture and the whole is homogenized. After storage for 48 hours at ambient temperature, crystals of anhydrous form D appeared. The amount of crystallized product recovered by filtration is approximately 2.45 g.

A comparative stability study was carried out between the acetone solvate form A and the anhydrous form D. The comparison of the PXRD analyses carried out on the A and D forms immediately after production and after having maintained said forms at 40° C. for one month gives the following results:

Form A: partial desolvation resulting in a mixture of the acetone solvate form A and of the anhydrous form B being obtained.

Form D: no change detected after maintaining at 40° C. for one month.

The invention claimed is:

1. Crystalline anhydrous form D of 4-acetoxy-2α-benzoyloxy-5β,20-epoxy-1-hydroxy-7β,10β-dimethoxy-9-oxotax-11-en-13α-yl (2R,3S)-3-tert-butoxycarbonylamino-2-hydroxy-3-phenylpropionate, characterized by a PXRD diagram exhibiting characteristic lines located at 3.9, 7.7, 7.8, 7.9, 8.6, 9.7, 10.6, 10.8, 11.1 and 12.3±0.2 degrees 2-theta.

* * * * *

UNITED STATES PATENT AND TRADEMARK OFFICE
CERTIFICATE OF CORRECTION

PATENT NO. : 8,378,128 B2  
APPLICATION NO. : 12/837559  
DATED : February 19, 2013  
INVENTOR(S) : Pascal Billot et al.

Page 1 of 1

It is certified that error appears in the above-identified patent and that said Letters Patent is hereby corrected as shown below:

In the Specifications:

In column 1, line 8, delete "3 S" and insert -- 3S --, therefor.

In column 1, line 16, delete "antileukaemic" and insert -- antileukemic --, therefor.

In column 1, line 45, delete "calorimetry" and insert -- Calorimetry --, therefor.

In column 3, line 48, delete "calorimetry" and insert -- Calorimetry --, therefor.

In column 4, line 6, delete "28," and insert -- 2θ, --, therefor.

Signed and Sealed this  
Eighteenth Day of June, 2013

Teresa Stanek Rea  
*Acting Director of the United States Patent and Trademark Office*